United States Patent [19]
McLeod et al.

[11] Patent Number: 6,146,586
[45] Date of Patent: Nov. 14, 2000

[54] DUAL CURRENT METHOD AND APPARATUS FOR STERILIZATION OF MEDICAL DEVICES

[75] Inventors: Bruce R. McLeod; J. William Costerton, both of Bozeman, Mont.

[73] Assignee: The Research and Development Intstitute, Bozeman, Mont.

[21] Appl. No.: 09/084,959

[22] Filed: May 28, 1998

[51] Int. Cl.[7] ................................................. A61L 2/03
[52] U.S. Cl. ........................ 422/23; 422/300; 204/272; 204/287; 204/297 R; 204/297 W
[58] Field of Search .............................. 422/22, 23, 28, 422/292, 300; 204/554, 660, 272, 287, 297 R, 297 W

[56] References Cited

U.S. PATENT DOCUMENTS

| | | | |
|---|---|---|---|
| 3,963,438 | 6/1976 | Banez . | |
| 4,282,179 | 8/1981 | Gunther | 422/27 |
| 4,419,248 | 12/1983 | Costerton | 210/764 |
| 4,542,169 | 9/1985 | Costerton | 523/121 |
| 4,579,597 | 4/1986 | Sasa et al. | 134/21 |
| 4,800,959 | 1/1989 | Costerton et al. | 166/246 |
| 5,090,433 | 2/1992 | Kamaga | 134/169 C |
| 5,137,689 | 8/1992 | Cantrell | 422/28 |
| 5,174,378 | 12/1992 | Costerton et al. | 166/246 |
| 5,184,601 | 2/1993 | Putman | 128/4 |
| 5,240,675 | 8/1993 | Wilk et al. | 422/22 |
| 5,312,813 | 5/1994 | Costerton et al. | 514/29 |
| 5,462,644 | 10/1995 | Woodson | 204/131 |
| 5,551,462 | 9/1996 | Biermaier | 134/166 C |
| 5,637,877 | 6/1997 | Sinofsky | 422/24 |
| 5,682,199 | 10/1997 | Lankford | 348/72 |
| 5,695,447 | 12/1997 | Yabe et al. | 600/121 |
| 5,714,119 | 2/1998 | Kawagoe et al. | 422/21 |

FOREIGN PATENT DOCUMENTS

| | | |
|---|---|---|
| WO 87/03261 | 6/1987 | WIPO . |
| WO 92/19286 | 11/1992 | WIPO . |

*Primary Examiner*—Elizabeth McKane
*Attorney, Agent, or Firm*—McDermott, Will & Emery

[57] ABSTRACT

In order to completely sterilize all of the surfaces of a medical instrument on which biofilms are apt to form, the device is immersed in a container containing an antibiotic solution in a manner wherein all of the contaminated surfaces are forced into intimate contact with the antibiotic solution. A first current is applied to a first electrode disposed at one end of the container to establish a first current flow about the exterior of the instrument between the first electrode and a second distal electrode which is either proximate or in direct contact with an end portion of the device. A second current is passed between a third electrode which is either in electrical contact with a part of the instrument that is not immersed in the antibiotic solution, or immersed in the solution has been forced into the interior of the device, and the second electrode via a second current path which extends through the interior of the instrument. The two currents are applied for a predetermined time selected to achieve the sterilization of any biofilms which have formed.

19 Claims, 6 Drawing Sheets

DUAL CURRENT METHOD AND APPARATUS FOR STERILIZATION OF MEDICAL DEVICES

BACKGROUND OF THE INVENTION

1. Field of the Invention

The present invention relates generally to a method and apparatus for sterilizing medical instruments, such as proctoscopes, and the like. More specifically, the present invention relates to a method and apparatus which utilizes electric current to sterilize medical instruments, such as proctoscopes, that have elongated tubular structures with interior surfaces on which stubborn and/or hard to clean biofilms are apt to form.

2. State of the Prior Art

Modern medical instruments which are used for exploratory or interdiction/surgical purposes within the human body require sterilization and/or cleaning between uses. In the case of exploratory devices such as proctoscopes, which are used for early detection of colon cancer, for example, careful cleaning between uses is required. Current practice, however, does not involve complete sterilization of proctoscopes between uses. Instead, a so-called "alcohol" cleaning is used. The reason for this resides in the manner in which this type of device is constructed. That is to say, there is usually at least one small internal tube running the full length of the proctoscope, which renders it virtually impossible to get alcohol, for example, into contact with all of the interior surfaces of the tube(s), and thus effectively attempt to kill all of the bacteria.

The construction of the proctoscope further precludes the use of normal heat sterilization (e.g. autoclaving) inasmuch as important elements are made of a plastic which does not exhibit sufficient resistance to elevated temperatures. However, even if it were to be possible to autoclave the device, the time required for sterilization would render it virtually impossible for a physician to use the device more than once a day.

U.S. Pat. No. 5,462,644 issued to Woodson on Oct. 31, 1995, discloses a method of killing microorganisms which form a biofilm on the surfaces of medical articles or on tissue or implant surfaces in a living subject. This sterilization is achieved by applying an electric field to an electrically conductive medium (viz., electrolyte) in which the biofilm is immersed.

The electrically conductive medium here includes a biocide or is capable of generating a biocide in situ upon application of the electric field. One example of the Woodson technique involves immersing an instrument such as a catheter, for example, in a bath having electrodes arranged at either end. The solution in which the catheter is immersed contains a suitable electrolyte and further can contain a sterilant such as glutaraldehyde.

While the woodson arrangement is claimed to have met with some success in the area of efficient cold sterilization, in the instance the medical instrument takes the form of a proctoscope, the process has met with only limited success due to the internal passage structure which is inherent with this type of device.

U.S. Pat. No. 5,312,813 issued to Costerton et al. issued on May 17, 1994, discloses a biofilm reduction method, which also involves the production of an electric field across the surface containing the biofilm which is subject to sterilization.

Another example of this type of sterilization arrangement is illustrated in the PCT patent application publication no. WO 92/19286. However, this arrangement, like those mentioned above, has not been particularly successful when applied to the sterilization of devices such as proctoscopes, which have elongated, small diameter, internal passage structures.

SUMMARY OF THE INVENTION

It is a general object of the present invention to provide a sterilization technique by which medical devices can be quickly and efficiently sterilized.

A more specific object of this invention is to provide a method and apparatus for sterilizing instruments that have elongated internal conduit structures which are inaccessible to conventional scrubbing tools and techniques and which have components made of materials that cannot withstand high temperatures.

It is a further object of the present invention to provide an arrangement via which a proctoscope or similar medical instrument can be quickly and easily disposed and subsequently sterilized within a short period of time, and thus permit repeated use of the device on multiple patients, at short time intervals during the course of a day.

It is a further object of the invention to provide a method of sterilization which is particularly applicable to medical instruments, such as proctoscopes, and which can be applied quickly and easily and permit sterilization to be carried out in a period of about 20 to 240 minutes duration.

Additional objects, advantages, and novel features of the invention shall be set forth in part in the description that follows, and in part will become apparent to those skilled in the art upon examination of the following or may be learned by the practice of the invention.

In brief, the above objects can be achieved by a technique wherein, in order to completely sterilize all of the surfaces of a medical instrunent on which biofilms are apt to have formed, the device is immersed in a liquid electrolyte medium, which may be a solution containing an antibiotic or biocide, in a manner wherein the liquid electrolyte is forced into contact with the contaminated surfaces that are inside the device as well as being in contact with contaminated surfaces that are outside the device. A first electric current is established between a first electrode disposed in the liquid electrolyte in the container outside the device and a second distal electrode which is also disposed in the electrolyte in a position that is remote from the first electrode and is either proximate or in direct contact with the device. A second current is established between a third electrode (or suitable connection) disposed in the liquid electrolyte inside the device and either the second electrode or a fourth electrode that is disposed in the electrolyte either proximate or in direct contact with the device. The two currents are applied either simultaneously or sequentially for sufficient time to achieve the sterilization of biofilms on the device, including inside tube or interior wall surfaces as well as external surfaces of the device. In devices that have a metal tube forming the inside surfaces, the metal tube can be the third electrode, and the second electrode (alternatively, a separate fourth electrode) can be either in direct contact with the tube or spaced a distance apart from the tube.

More specifically, a first aspect of the present invention resides in a method of sterilizing outside surfaces and inside surfaces of an instrument comprising the steps of: immersing the instrument in a liquid electrolyte medium that may be a solution containing an antibiotic or biocide in proximity to a first electrode positioned in the liquid electrolyte outside the instrument; and either in contact with or in proximity to a second electrode that is also positioned in the liquid electrolyte remote from the first electrode; establishing a first current path between the first and second electrodes; interconnecting a third electrode positioned in the liquid electrolyte inside the instrument to either the second electrode or a fourth electrode positioned in the liquid electrolyte outside the instrument to establish a second path; passing a first current through the first current path; passing a second current through the second current path; and maintaining the passage of the first and second currents through the first and second current paths for a predetermined time.

An additional feature of the above method is that the step of immersing can include pressuring the liquid electrolyte so as to force the liquid electrolyte into contact with the surfaces of the instrument which require sterilization. Such pressurization is particularly useful to force the liquid electrolyte into contact with interior surfaces inside the instrument to achieve more thorough sterilization.

Another feature of the above mentioned method is the step of arranging the first electrode to surround a portion of the instrument which is immersed in the antibiotic solution at a location is distal from the second electrode and thus establish the first current path surrounding the external surface of the device.

Still another aspect of the invention resides in an apparatus for sterilizing an instrument comprising: a container having an opening, the container containing a liquid containing an antibiotic; a seal disposed at the opening of the container said seal having a shape and size that permits the insertion of the instrument into the container and establishes fluid-tight seal about the periphery of the instrument and prevent fluid communication between the interior of the container and the exterior of the container around the periphery of the instrument; a first electrode disposed in the liquid in a first portion of the container outside the instrument; a second electrode disposed in the liquid in a second portion of the container spaced a distance apart from the first electrode and adapted to be either proximate to, or in contact with, an end of the instrument upon insertion of the instrument through the sale and into the container; a first electrical circuit electrically interconnecting the first and second electrodes, the first electrical circuit including a first power source for selectively applying voltage across the first and second electrodes to cause a current to flow in a first current path through the liquid between the first and second electrodes outside the instrument; and a second electrical circuit, the second electrical circuit including a third electrode which can be, but is not necessarily, a portion of the instrument, the second electrical circuit being electrically connected with the second electrode and including a second power source for selectively supplying a current through a second current path which extends from the third electrode, through the instrument, to the second electrode.

The above mentioned apparatus is such as to include an internal passage structure in the instrument into which the liquid containing the antibiotic is forced as the instrument is inserted into the container, and wherein the second current path extends through the internal passage structure of the instrument.

A third aspect of the invention resides in an apparatus for sterilizing an instrument comprising: means for immersing a portion of the instrument in a liquid containing an antibiotic in a manner wherein at least a portion of the liquid is pressurized and forced into cavities within the instrument; means for passing a first current along a first current path which extend through the liquid surrounding the exterior of the instrument to an electrode which is proximate a portion of the instrument which is immersed in the liquid; and means for passing a second current through the instrument to the electrode along a second current path which extends through the interior of the instrument.

Another aspect of the invention resides in a method for sterilizing an instrument comprising the steps of: immersing a portion of the instrument in a liquid containing an antibiotic in a manner wherein at least a portion of the liquid is pressurized and forced into cavities included in the instrument, passing a first current through the liquid surrounding the instrument, to an electrode which is proximate portion of the instrument that is immersed in the liquid; and passing a second current through either of both of the instrument and the liquid, to the electrode in contact with the instrument.

The invention resides in both immersing the exterior and filling the inner cylinder of the proctoscope with antibiotic solution, and then achieving a full sterilization by applying two separate electric currents to/through the structure. The currents are preferably dc currents, but are not necessarily limited thereto.

These two currents establish two current flows, one current flow that passes through the interior of the device and the other current flow which flows about the exterior. The first current of between 2 and 10 milliamperes is induced to flow in the liquid antibiotic that surrounds the outside of the proctoscope. The second current of between 2 and 10 milliamperes is induced to flow through or over the material that forms the inner cylinder of the proctoscope and/or the liquid antibiotic that fills the spaces/cavities within the inner cylinder.

The liquid antibiotic used for sterilization contains from 2–10% and more preferably about 5% (five parts per hundred by volume) glutaraldehyde solution. The combined action of a dc current and a 2 percent antibiotic solution have been shown to accomplish, in 15 to 240 minutes, a 99.9999 percent kill of the bacteria in any bacterial biofilm that potentially could have formed on any exposed surface of the proctoscope.

It is necessary, if the kill is to be accomplished, for the liquid antibiotic to completely surround the outside surface that is to be sterilized and to completely fill the inner cylinder that goes up the inside of the proctoscope. It is easy to accomplish the first of these requirements, but, since the inner cylinder of a typical proctoscope has a very small diameter, care must be taken to ensure that the conduit through the cylinder as well as other small cavities/passages that might or might not be in the instrument in which capillary action is apt to take place all get completely filled with liquid antibiotic as the proctoscope is loaded into the sterilization device.

As discussed above, current practice involves either cleaning the outside of the proctoscope using an alcohol "wipe down" or soaking the proctoscope in a disinfectant bath for several hours. Bacterial biofilms are not susceptible to the alcohol wipe down unless vigorous scrubbing of the colonized surface is carried out thus destroying the biofilm via abrasive action, nor are they particularly susceptible to liquid antibiotics unless the concentration of the antibiotic is extremely high. Even the prolonged soaking of the proctoscope in an antibiotic bath will not assure a sterile device since the lumen of the inner tube, on which bacteria are highly apt to colonize and form a biofilm, is of such a small diameter that it is unlikely that the entire inner surface is reached by the liquid antibiotic during the soak. Studies have been done on these devices that show that a considerable amount of dried foreign matter is often found just inside the distal end of the inner tube of the proctoscope.

An embodiment of the invention via which this problem is solved, includes the filling the inner tube by forcing the proctoscope into a liquid antibiotic filled chamber which is provided with a seal. More specifically, as the proctoscope enters this chamber through an upper port that contains an O-ring which provides a fluid tight seal against the exterior of the proctoscope, fluid (viz., air or liquid) is prevented from leaking out as the proctoscope is forced into the cylinder. Since the proctoscope displaces an increasing volume of liquid, the hydraulic pressure which is accordingly generated will force the liquid antibiotic up into the small diameter passage or passages in the inner tube. The rate at which the inner cylinder of the proctoscope fills can be adjusted by choosing the volume of the chamber and the head space (the amount of air, if any, above the antibiotic liquid prior to insertion of the proctoscope into the sterilization chamber) of the sterilization chamber and the rate of movement of the proctoscope into the sterilization chamber. The construction of the proctoscope is such that excess liquid forced into the inner tube can exit and be drained away from an outlet in an upper portion of the inner tube as the proctoscope is forced into the sterilization chamber. The final position of the proctoscope in the sterilization chamber is preferably such that the inner tube either contacts or is positioned in close proximity to an electrically grounded metal stud electrode at the lower end of the sterilization chamber. The sterilization chamber is preferably dimensioned to allow the working length of the proctoscope (about 180 centimeters) to be immersed in the sterilizing liquid in the chamber.

When the proctoscope is in place in the sterilization chamber, two, independent power supplies (preferably, but not necessarily dc power supplies) are connected to the chamber. The positive terminal of power supply number (1) is connected to the antibiotic liquid surrounding the outer surface of the proctoscope by means of a suitable electrode made of stainless steel for example. The electrode can be simply a short length of conducting wire extending into the liquid or, alternatively, is a thin annular or collar-like band of stainless steel that is mounted in the sterilization chamber in a manner that at least partially, if not completely, surrounds outside of the proctoscope.

The negative terminal of this power supply number (1) is electrically connected to the metal stud at the opposite end of the sterilization chamber. The purpose of these electrical contacts is to set up a flow of current in the liquid antibiotic along and over the full length (that is from top to bottom) of the external surface of the proctoscope. The power supply is adjusted to cause between 3 and 10 mA to flow in the liquid antibiotic solution.

The positive terminal of the second power supply is electrically connected to the upper end of the inner tube of the proctoscope, which, if it is metal as in typical proctoscopes, functions as an electrode that is in electrical contact with the liquid antibiotic that is forced into the inner tube. Alternatively, an electrode can be inserted into the tube through any suitable opening, such as via the outlet through which excess antibiotic liquid overflows, in a manner wherein contact with the liquid is established. The negative terminal of the second power supply is electrically connected preferably to the metal stud at the lower end of the sterilization chamber although another electrode in the lower end of the sterilization chamber could also be used. This arrangement causes current to flow through the inner tube, if the inner tube is metal, or through the antibiotic liquid in the inner tube of the proctoscope, or both. Again, the current from the second power supply is adjusted to a preferable range between 2–10 mA.

The result of allowing these currents to flow in the sterilization chamber for between 15 minutes and 240 minutes will result in the killing of approximately 99.9999% of any bacteria present on the proctoscope. For most bacteria that one would expect to find on or in the proctoscope, it is expected that this kill percentage will be accomplished in less than 30 minutes.

BRIEF DESCRIPTION OF THE DRAWINGS

Various features and advantages of the present invention will become more clearly appreciated as a description of the sterilization method and the structure which is used to achieve the sterilization, are given with reference to the appended drawings wherein.

In the Drawings.

DETAILED DESCRIPTION OF THE PREFERRED EMBODIMENTS

Figure 1:
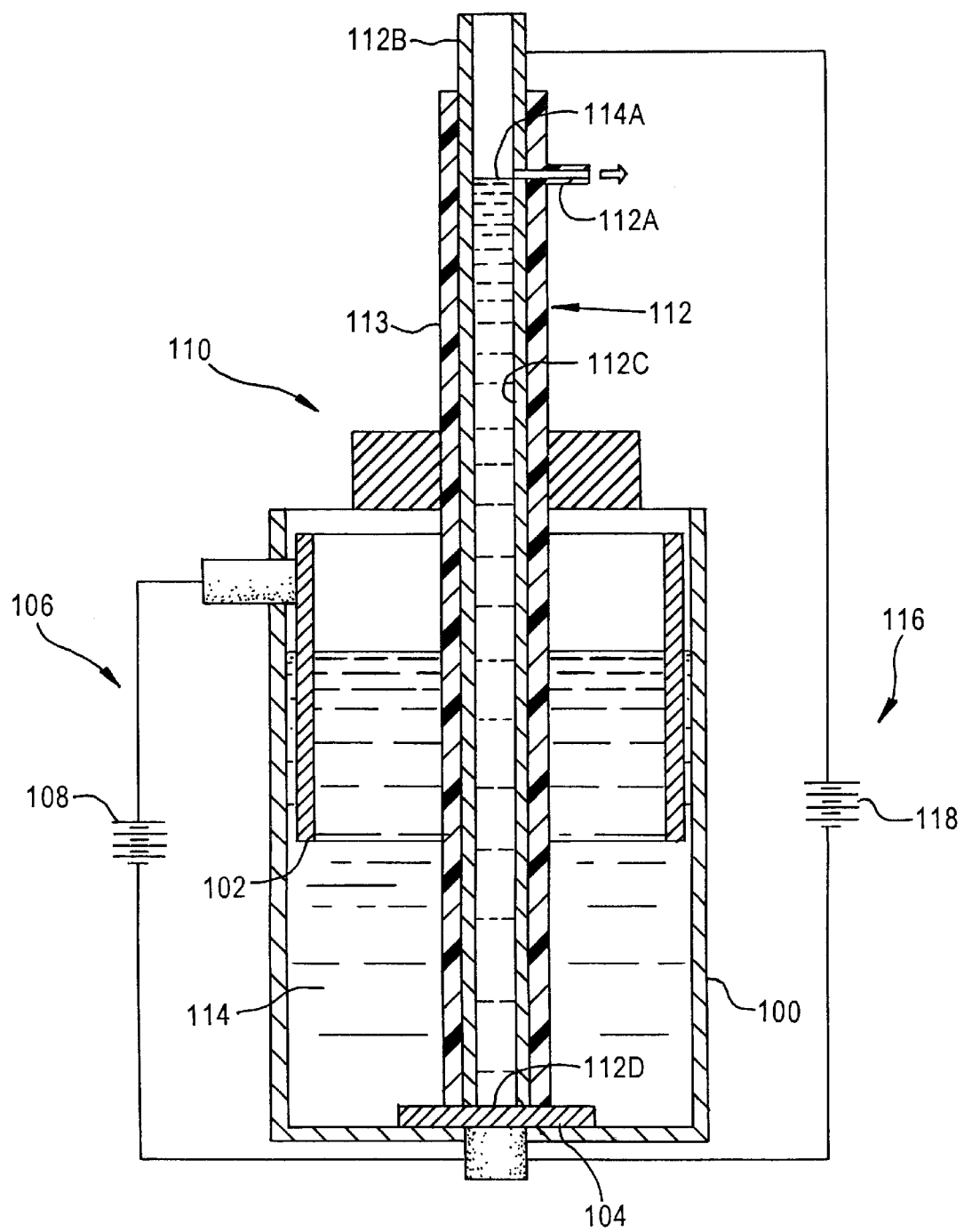
FIG. 1 is a schematic cross-sectioned representation of a device used for sterilizing proctoscopes.

One embodiment of the invention is depicted diagrammatically in FIG. 1. In this arrangement, a special device is used to implement the sterilization method according to the present invention. This device includes a container 100 that forms a sterilization container in which a first electrode, which is preferably, but not necessarily, an annular sleeve-like anode 102 and a second electrode, which is preferably, but not necessarily, a stud-like cathode 104, are disposed. As shown, the annular sleeve-like anode 102 is disposed in the upper portion of the container 100, while the stud-like cathode 104 is arranged to be immediately adjacent the lower end or bottom of the container 100. The anode 102 and the cathode 104 are, in this embodiment, connected by an electrical circuit generally denoted by the numeral 106. This circuit 106 includes a source 108, which, for the sake of illustration, is shown schematically as a dc battery, but which can be any suitable power source, as would be obvious to persons skilled in the art. In this embodiment, the dc source 108 is arranged for example, but not for limitation, to produce a current in a range of about 2–10 mA at a voltage in a range of about 0.5–20 volts. Of course, the source 108 could be reversed in polarity so that the first electrode 102 is a cathode and the second electrode 104 is an anode, or the source could be AC.

The upper end of the container 100 is provided with an annular sealing arrangement 110, such as an O-ring or the like. This annular seal 100 is so dimensioned and shaped as to permit a device or instrument generally denoted by the numeral 112, to be inserted therethrough in a manner which produces a fluid-tight seal. The device 112 illustrated in FIG. 1 depicts, for example, a proctoscope that typically has a metal inner tube 112B mounted in a plastic housing 113. The inner tube 112B has an interior passage 112C with an opening 112D at one end of the proctoscope 112. The plastic housing 113 is non-electrically conductive, although this invention is applicable to and would work with a medical instrument that has a conductive housing. The inner tube 112B is electrically conductive and can function as an electrode used to establish a current path for this invention, although it does not have to be connected to function as an electrode for purposes of this invention,. as illustrated and explained below.

Prior to the insertion of the device, the container 100 is suitably filled with an electrolyte solution 114 which can, but does not have to, contain a predetermined amount of antibiotic, for example, a glutaraldehyde solution in a concentration of about 5 parts per 100 by volume.

As the device 112 is inserted through the seal 110, the communication between the interior of the container 100 and the exterior of the container 100 is cut off. Therefore, as the device 112 is forced into the container 100, the volume of the device 112 displaces liquid in the container, which cannot escape through the seal 110, so the pressure within the container 100 rises generating a hydraulic pressure which causes some of the solution 114 to be forced up into and through the interior of the proctoscope, as indicated at 114A. As will be appreciated, with this type of fluid displacement, the interior, in particular the inner tube 112B and any associated cavities and passages, become filled with the antibiotic containing liquid 114A. Excess liquid can be permitted to overflow from the interior of the tube 112B via a port 112A in the upper portion of tube 112B.

Figure 2:
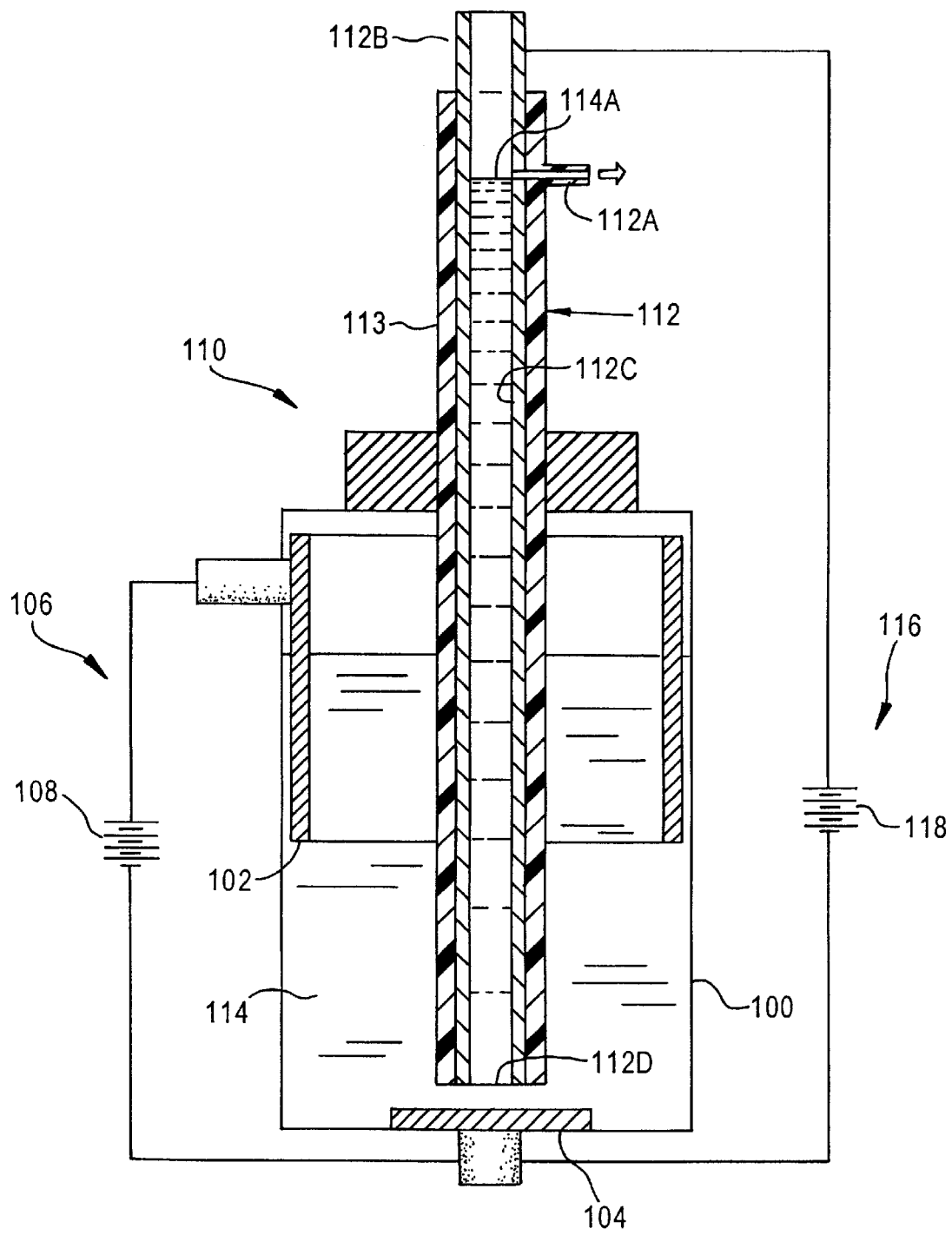
FIG. 2 is a schematic cross-sectioned view similar to FIG. 1, but with the bottom end of the proctoscope positioned above and not in electrical contact with the bottom electrode.

The device 112 is inserted into the container 100 preferably until such time as the lower end either contacts or closely proximates the cathodic stud 104 at the bottom of the container 100. Following this, an electrical connection with the inner cylinder 112B of the proctoscope is established in a manner which completes a second dc circuit arrangement 116 between the cathodic stud 104 and the inner cylinder 112B. In this instance also, the dc source 118 of the second dc circuit 116 is a schematically depicted for convenience simply as a battery, although other power sources can also be used. As shown in FIG. 1, when the inner tube 112B of the instrument 112 is metal and is positioned with its lower end in contact with the stud 104, there is a direct electrical connection for a current path established between the inner tube 112B and the stud 104. Alternatively, if the metal inner tube 112B is positioned with its lower end proximate, but not touching stud 104, as shown in FIG. 2, then the current path between the stud 104 and the inner tube 112B will be through a portion of the liquid 114. Of course, if the inner tube 112B is not metallic, the current path from stud 104 will be through liquid 114 regardless of whether inner tube 112B contacts stud 104. Of course, either the external circuit 106 or the internal circuit 116 can also be used independent of each other. It will of course be understood by persons skilled in the art that further controls can be included in the circuits to permit the current to be selectively switched on/off and or selectively adjusted in amplitude, although such controls are not considered to form this invention. It is, of course, also possible to program the application of the voltage/amperage with respect to time if such should be considered desirable/ effective, but which is also no considered to form this invention.

Once the proctoscope 112 has been suitably disposed within the container 100 and filled with the antibiotic containing liquid 114, the first and second electrical circuits 106, 116 are energized so as to pass a first current between the annular sleeve-like anode 102 and the stud-like cathode 104; and a second current to the stud-like anode 104 via the inner cylinder 112B of the proctoscope 112 or via the liquid 114A in the inner tube 112B, or both. In this embodiment both of these currents are preferably dc currents in a range of about 2 and 10 milliamperes and with voltages in a range of about 0.5–20 volts.

The arrangement of the annular sleeve-like anode 102 is such as to ensure that the effect of the current flow through the solution 114 outside the proctoscope 112 is such as to produce the required biocidal effects over the whole external surface of the proctoscope 112, while the second circuit 116 causes current to flow from inner tube 112B and/or through the liquid 114A in inner tube 112B to cathode stud 104 and thus ensure that current is effectively used in these connections. The combination of the annular anode 102 and the centrally located stud-like cathode 104, are considered to be an effective arrangement which allows for the ready insertion of the instrument to be cleaned, into a position wherein effective current flow is ensured and which further facilitates the second flow of current through the interior of the instrument proper.

Upon the elapse of a predetermined period of time, which can be set between 15 and 240 minutes, the application of the first and second currents can be terminated and the proctoscope 112 can be removed from the container 100, rinsed, and dried to be made ready for use.

It will be noted at this point that the dimensions of the container shown in FIG. 1, are not indicative of the actual size of the container utilized in accordance with the present invention, anc that the entire arrangement of FIG. 1, including the medical instrument 112 and the container 100, is schematic and has been presented in diagrammatic form for illustrative simplicity only. The medical instruments, such as proctoscope 112, are conventional and commercially available, and persons skilled in the art can make the container 100 with known materials and techniques, once the purposes and functions of the invention are learned from this disclosure.

Figure 3:
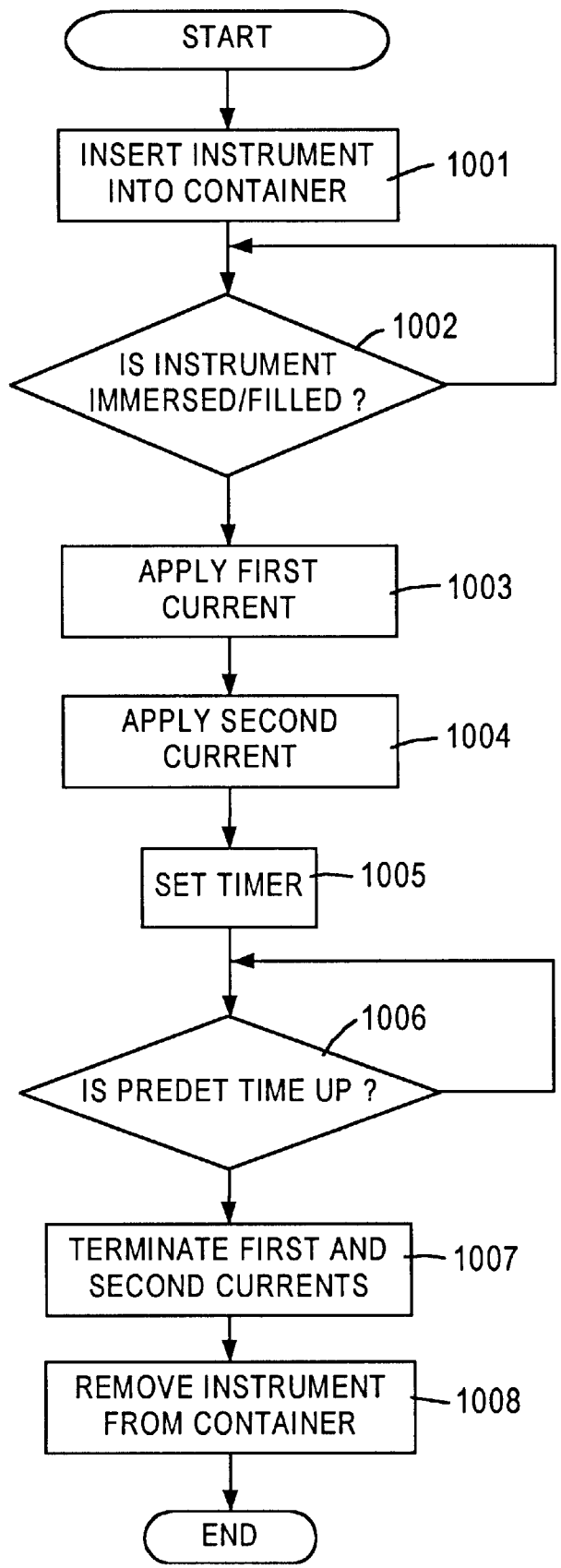
FIG. 3 is a flow chart depicting the steps which characterize the sterilization method according to the present invention.

FIG. 3 shows in flow chart the process which has been outlined above. That is to say, at step 1001, the instrument 112 is inserted in the container 100 containing the antibiotic material. At step 1002, it is determined whether the instrument is properly immersed and/or filled with the antibiotic solution. There are myriad ways to determine when the inner tube of the instrument is filled, one of the simplest being direct observation of liquid running out of the outlet 112A in FIG. 1. When this situation is ascertained, the process proceeds to steps 1003–1005, wherein the first and second currents are applied for a predetermined time. At step 1006, the expiration of the predetermined time is determined and at steps 1007 and 1008, the current supplies are terminated and the instrument or device is removed from the container.

As pointed out above, if a current of approximately 100 milliamperes is applied through both of the first and second electric circuits, the effect of the 5% antibiotic solution is such as to accomplish a 99.9999% kill of the bacteria in any bacterial biofilm that may have formed within or on the device. Experiments have shown that the application of the two dc currents for a period of about 30 minutes is sufficient top achieve the above mentioned level of sterilization.

There are numerous ways in which the concepts and principle features of this invention can be implemented. Several alternative embodiments of such implementations are described below for example, but not for limitation.

Figure 4:
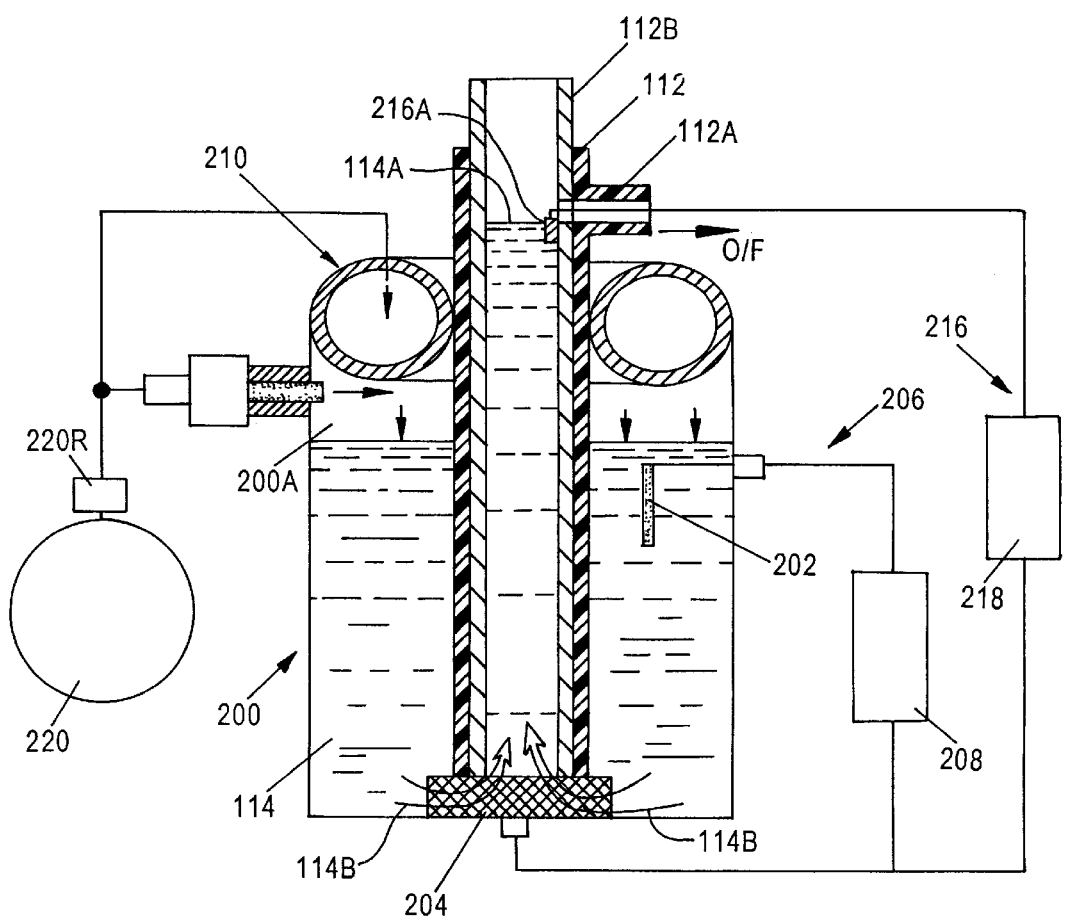
FIG. 4 is a schematic cross-sectional view of a second embodiment of the invention featuring an inflatable seal arrangement.

One such alternative embodiment of the invention is shown in FIG. 4. In this arrangement, the O-ring sealing arrangement 110 of the first embodiment is replaced with an inflatable toroidally-shaped seal arrangement 210 which can be selectively inflated using air from a source generally denoted by the numeral 220 to form the seal around the periphery of instrument 112 as well as to pressurize the liquid 114 to force a portion 114A of the liquid 114 into the inner tube 112B of the instrument 112. This source 220 can take the form of a pump, or a container of gas under pressure such as air. The pump can be electrically driven or is preferably a manually squeezable bulb of the nature commonly used with blood pressure measuring apparatus. This latter type of arrangement is usually provided with a vent or relief valve 220R, which allows the pressure to be relieved when desired.

It is to be noted that the use $CO_2$ under pressure should be avoided to pressurize the interior of the vessel and to force a little of the antibiotic liquid in the container to pass up through the inner tube 112B of the device and to overflow through the outlet 112A, as $CO_2$ tends to be very soluble in water and could form bubbles that keep the antibiotic liquid from contacting parts of the instrument 112 and thereby inhibit complete sterilization of all the surfaces.

It is also deemed advantageous to throttle the supply of gas to the interior of the container 200 using a orifice or the like to ensure that the pneumatic tire-like arrangement 210 is rapidly inflated and engages the sides of the device 112, whereafter the pressure can smoothly build-up the air space 200A defined above the liquid surface to force the liquid 114A into the inner tube 112B until it overflows through the outlet 112A.

Another difference resides in that the stud-like cathode 204 in this embodiment is made of wire mesh to permit unrestricted flow of liquid 114 into the inner tube 112B of the device 112 in the manner depicted by the flow arrows 114B. The mesh also increases the effective surface area of the electrode and ensures that both the current paths can be readily established.

As will be appreciated, once the inflatable seal arrangement 210 has sealingly engaged the sides of the device 112 and a fluid-tight seal is produced, the pressure which develops in the air space 200A is such as force the liquid containing the antibiotic up into the passage structure(s) 112B within the device 112.

With this configuration, an operator can lower the device 112 into the vessel until it seats on, or is in proximity to, the wire mesh cathode 204, and then manually operate the valve/bulb to inflate the seal 210 and subsequently pressurize the interior of the container 200. After some fluid is observed to overflow from port 112A in the manner indicated by arrow O/F, the operator can terminate the supply of pressure, and then insert a lead 216A into the outlet port 112A so that an end portion thereof becomes immersed in the antibiotic fluid 114A which has been driven up into the interior of the device 112. This allows current to be passed down through the antibiotic liquid 114, which, as mentioned above, also functions as an electrolyte, through the device to the mesh electrode 204 which is located at the bottom of the vessel 200. The current flows between the lead or electrode 216A and the mesh electrode 204 via the liquid electrolyte 114A inside the tube 112B, even in an instrument in which the tube 112B is not metallic, which is not the ordinary case, but is a possibility.

Merely by way of example, in this embodiment the electrode 202 in the upper portion of the vessel takes the form of one or more wires or flat plates (note that only one is shown for illustrative simplicity). This electrode could also be formed of a suitable wire mesh in the same manner as the anode 204 if so desired.

Figure 5:
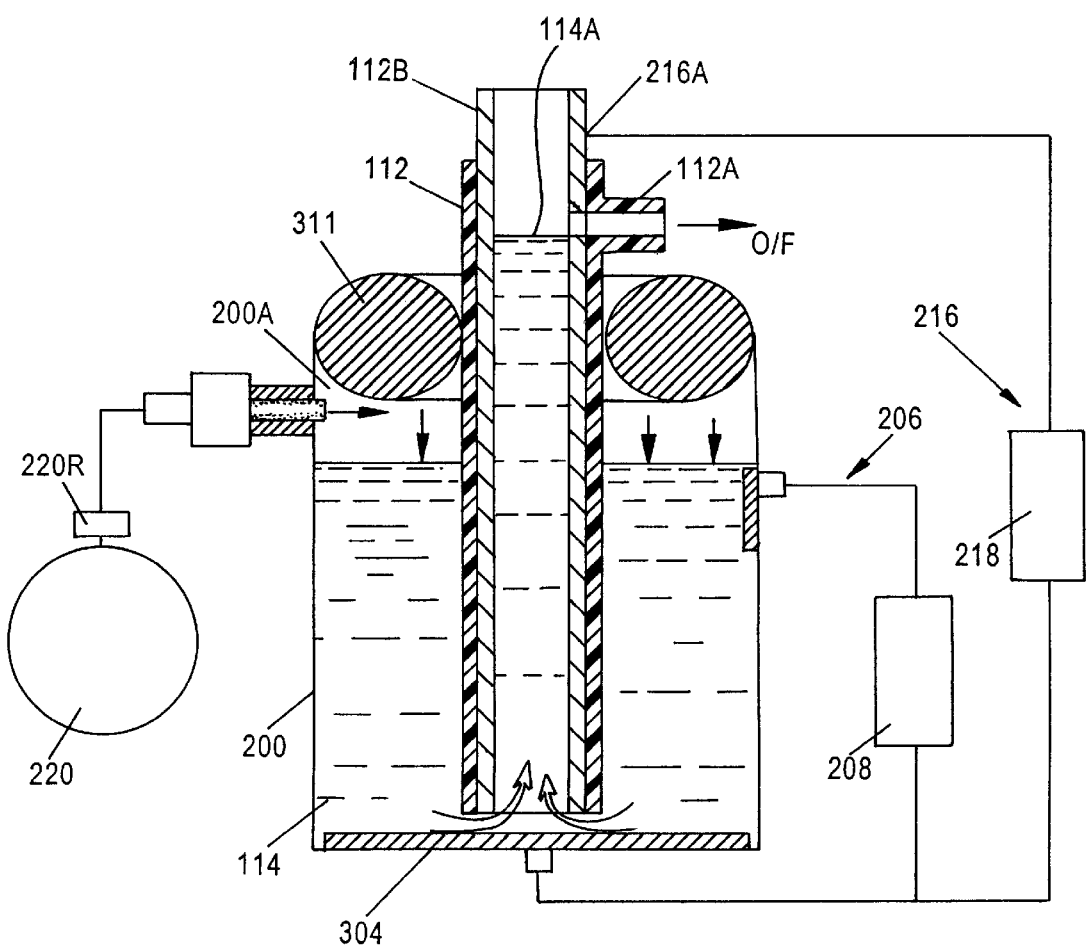
FIG. 5 is a schematic cross-sectional view of a third embodiment of the invention.

FIG. 5 shows a further embodiment of the invention. In this arrangement, the inflatable seal is replaced with a solid O-ring 311. Otherwise, this arrangement is basically similar to that shown in FIG. 4 with the exceptions that the cathode 304 in this embodiment takes the form of a plate; and the lead 216A is connected to a metallic portion of the device, such as the inner tube 112B, instead of being dipped into the liquid 114A within the device.

The provision of the solid O-ring 311, because of its initial rigidity, also facilitates the insertion of the device 112 to a position wherein the lower end of the device is spaced from the cathode 304 to permit unrestricted communication of the interior passage structure of the device 112 with the liquid 114 in the vessel 200. As described above, the second current path in this embodiment flows between metal inner tube 112B and cathode 304 via the liquid 114 that is between those two components.

Figure 6:
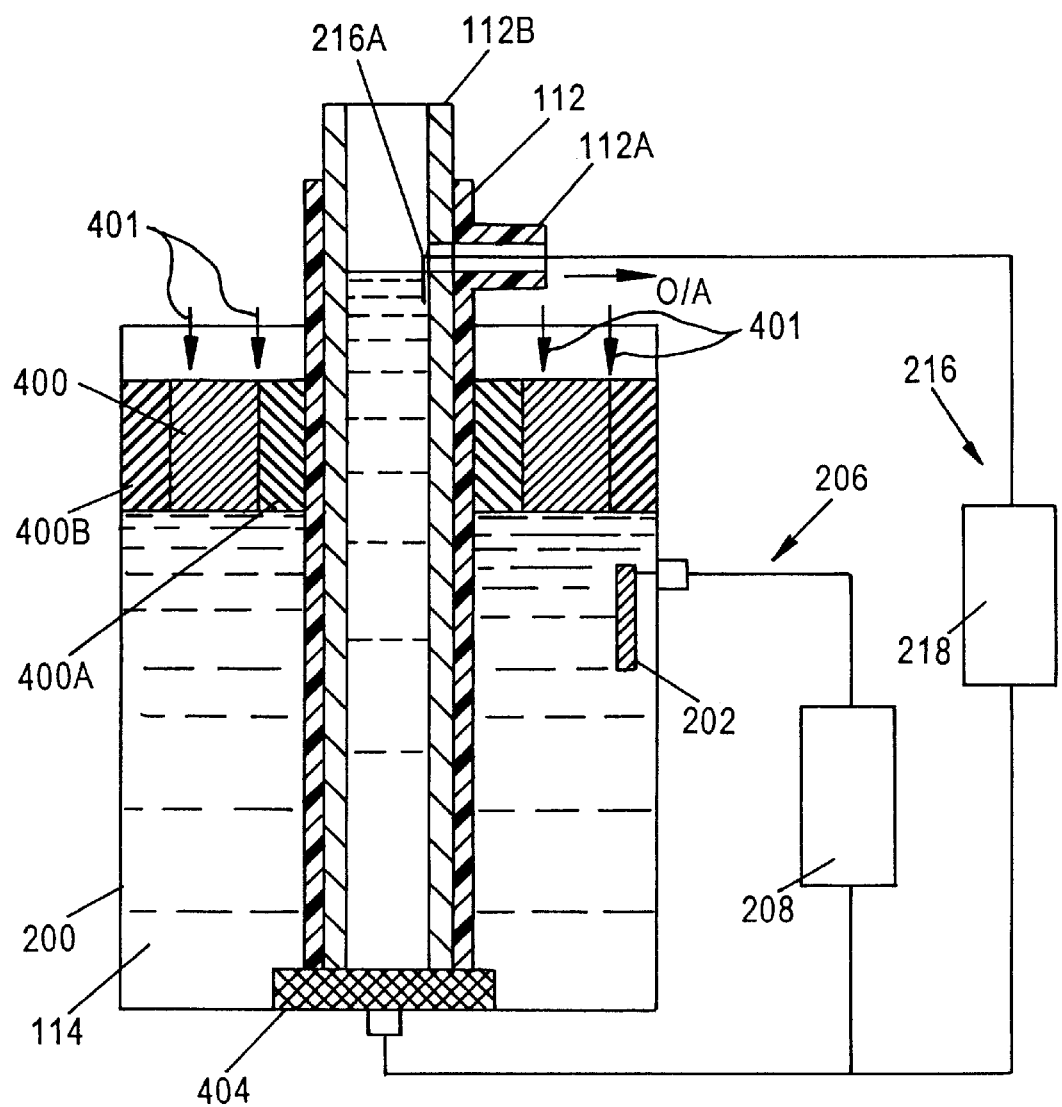
FIG. 6 is a schematic cross-sectional view of a fourth embodiment.

FIG. 6 shows a further variant wherein a piston 400 is disposed in the mouth of the container 200 and arranged to have a first annular inboard sealing member 400A in sealing engagement with the exterior periphery of the device 112, and a second outboard seal 400B which sealingly engages the wall of the container 200. By forcing the piston 400 down as indicated by arrows 401, it is possible to force antibiotic liquid 114 up into the interior of the device 112, as indicated at 114A, in manner similar to the other embodiments described above.

As will be appreciated, it is not essential that the lower end of the instrument 112 or even the lower end of the inner tube 112B actually contact the lower electrode (cathode 404) even though the downward movement of the piston 400 is apt to result in such contact. The passage of ions over the inner and outer surfaces of the device (first and second current paths) in the present of the antibiotic is sufficient to achieve the desired biocidal effect and to achieve a very high level of sterilization.

It will of course be understood that the present invention is in no way limited to the use of the containers shown in FIGS. 1–6 and that other immersion techniques can be contemplated without departing from the scope of the invention. That is to say, any technique which provides an effective filling of the passages with the proctoscope can be contemplated, and any electrode and circuit arrangement can be used to produce the two current paths—one around the outside of the instrument 112 and the other through the interior of the instrument 112. For example, a pump not shown can also be used to force fluid through the interior of the proctoscope 112 while the proctoscope 112 is immersed in a container which is filled with antibiotic liquid and which has the electrodes disposed thereon, thus achieving a flushing action in addition to the sterilizing effect which results from the current flows. In fact, one of the electrodes could be disposed inside the conduit which leads from the pump to the device and which, merely by way of example, is fitted into or onto the port 112A of the device. This would ensure that a flow of ions would pass through the interior of the device toward the corresponding opposite polarity electrode immersed in the tank.

These and other variants, which will be evident to persons of skill in the art equipped with the preceding disclosure, are limited only by the appended claims.

What is claimed is:

1. A method of sterilizing an instrument comprising the steps of:
   immersing the instrument in an antibiotic solution;
   disposing a portion of the instrument in proximity to a first and second electrode;
   connecting a second electrode to a portion of the device and establishing a first current path between the first and second electrodes;
   immersing a third electrode in the antibiotic solution so as to be distal from the first electrode;
   interconnecting the third electrode and the second electrode to establish a second current path;
   passing a first current through the first current path;
   passing a second current through the second current path; and
   maintaining the passage of the first and second currents through the first and second current paths for a predetermined time.

2. A method of sterilizing as set forth in claim 1, wherein said step of immersing comprises the step of pressurizing the antibiotic solution so that intimate contact between the surfaces of the instrument which require sterilization and the antibiotic solution occurs.

3. A method of sterilizing as set forth in claim 1, further comprising the step of arranging the third electrode to surround a portion of the instrument which is immersed in the antibiotic solution and which is distal from the first electrode.

4. A method of sterilization as set forth in claim 1, further comprising the step of controlling the first current to have an amperage of 2–10 ma.

5. A method of sterilization as set forth in claim 4, further comprising the step of controlling the first current to have a voltage of 0.5–20 volts.

6. An apparatus for sterilizing an instrument comprising:
   a container having an opening, said container containing a liquid containing an antibiotic;
   seal means disposed at the opening of said container, said seal being arranged to permit the insertion of an instrument into the container and to establish a fluid-tight seal about the periphery of the instrument and prevent fluid communication between the interior of the container and an ambient atmosphere;
   a first electrode disposed in a first portion of the container;
   a second electrode disposed in a second portion of the container, said second electrode being distal from said first electrode and adapted to be proximate an end of the instrument upon its insertion into said container;
   a first electrical circuit electrically interconnecting the first and second electrodes, said first electrical circuit including a power source for selectively applying current across the first and second electrodes and through a first current path interconnecting the first and second electrodes; and
   a second electrical circuit, said second electrical circuit including a third electrode which is in contact with a portion of the instrument, said second electrical circuit being electrically connected with said second electrode and including a power source for selectively supplying a current through a second current path which extends from said third electrode, through the instrument, to said second electrode.

7. An apparatus as set forth in claim 6, wherein said instrument comprises a medical instrument and which includes an internal passage structure into which the liquid containing the antibiotic is forced as the instrument is inserted into said container, and wherein the second current path extends through the interior of the instrument.

8. An apparatus for sterilizing an instrument comprising:
   means for immersing a portion of the instrument in a liquid containing an antibiotic in a manner wherein at least a portion of the liquid is pressurized and forced into cavities within the instrument;
   means for passing a first current along a first current path which extends through the liquid solution surrounding the exterior of the instrument to an electrode which is proximate a portion of the instrument which is immersed in the liquid; and
   means for passing a second current through an interior passage structure of the instrument to the electrode along a second current path which extends through the interior of the instrument.

9. A method for sterilizing an instrument comprising the steps of:
   immersing a portion of the instrument in a liquid containing an antibiotic in a manner wherein at least a portion of the liquid is pressurized and forced into cavities included within the instrument;
   passing a first current through the liquid surrounding the instrument to an electrode which is proximate a portion of the instrument which is immersed in the liquid to effect sterilization of an exterior surface of the instrument; and
   passing a second current through an interior of the instrument to the electrode in contact the instrument to effect sterilization of an interior surface of the instrument.

10. A method of sterilizing a medical instrument that has a biofilm on an exterior surface and a biofilm on an interior surface comprising:
    immersing the exterior surface and the interior surface having the biofilms thereon in a liquid electrolyte;
    establishing a first electric current path along the exterior surface, and establishing a second electric current path along the interior surface; and
    passing a first electric current through the first current path, and passing a second electric current through the second current path.

11. The method of claim 10, including positioning the medical instrument in a container of the liquid electrolyte and applying sufficient pressure on the liquid electrolyte to force liquid electrolyte into contact with the interior surface that is to be sterilized.

12. The method of claim 10, including positioning a first pair of electrodes in the liquid electrolyte adjacent the exterior surface to establish said first electric current path and applying a first voltage across the first pair of electrodes to induce said first electric current to flow along the first electric current path, and including positioning a second pair of electrodes in the liquid electrolyte to establish said second electric current path and applying a second voltage across second pair of electrodes to induce said second electric current to flow along said second electric current path.

13. The method of claim 12, including arranging one of the electrodes of said first pair of electrodes to also be one of the electrodes of said second pair of electrodes.

14. Apparatus for sterilizing a medical instrument that has an elongated inner tube with a first end and a second end mounted in an elongated housing that has an external peripheral surface, wherein said elongated inner tube has an interior surface surrounding a passage with a first opening at said first end and a second opening at or adjacent the second end, comprising:

a container with a top end and a bottom end, said container having an aperture in said top end that is large enough to allow insertion of said medical instrument through said opening into said container;

liquid electrolyte in said container;

a first electrode disposed in said electrolyte adjacent said top end;

second electrode disposed in said liquid electrolyte adjacent said bottom end;

a voltage source connected to said first electrode and to said second electrode; and a second voltage source connected electrically to a third electrode in said passage and to a stud electrode disposed in said liquid electrolyte adjacent said bottom end of said container.

15. The apparatus of claim 14, wherein said third electrode is said inner tube.

16. The apparatus of claim 14, wherein said second electrode is said stud electrode.

17. The apparatus of claim 14, including a seal around said aperture in said top end that is sized and shaped to fit snugly enough around the external peripheral surface of the housing to prevent passage of fluid between said seal and said external peripheral surface at a pressure sufficient to force said liquid electrolyte in said passage to said second opening.

18. Apparatus for sterilizing a medical instrument that has an elongated inner tube with a first end and a second end mounted in an elongated housing wherein said elongated inner tube has an interior surface surrounding a passage with a first opening at said first end and a second opening at or adjacent the second end, comprising:

a container with a top end and a bottom end, said container having an aperture in said top end that is large enough to allow insertion of said medical instrument through said opening into said container;

liquid electrolyte in said container;

an external electrode positioned in said liquid electrolyte adjacent said bottom end;

a voltage source connected electrically to said external electrode, and a means for connecting said voltage source to an internal electrode in the passage.

19. The apparatus of claim 18, wherein said internal electrode is said inner tube.

* * * * *